(12) United States Patent
Babaev

(10) Patent No.: US 6,761,729 B2
(45) Date of Patent: *Jul. 13, 2004

(54) WOUND TREATMENT METHOD AND DEVICE WITH COMBINATION OF ULTRASOUND AND LASER ENERGY

(75) Inventor: Eilaz Babaev, Minnetonka, MN (US)

(73) Assignee: Advanced MedicalApplications, Inc., Eden Prairie, MN (US)

(*) Notice: Subject to any disclaimer, the term of this patent is extended or adjusted under 35 U.S.C. 154(b) by 75 days.

This patent is subject to a terminal disclaimer.

(21) Appl. No.: 10/366,787

(22) Filed: Feb. 14, 2003

(65) Prior Publication Data

US 2003/0153961 A1 Aug. 14, 2003

Related U.S. Application Data

(63) Continuation-in-part of application No. 09/745,943, filed on Dec. 22, 2000, now Pat. No. 6,533,803.

(51) Int. Cl.$^7$ ............................................. A61B 18/118
(52) U.S. Cl. ........................................ 607/89; 606/130
(58) Field of Search ...................... 606/41, 130; 607/89

(56) References Cited

U.S. PATENT DOCUMENTS

| | | |
|---|---|---|
| 3,275,059 A | 9/1966 | McCullough |
| 3,392,916 A | 7/1968 | Engstrom et al. |
| 3,561,444 A | 2/1971 | Boucher |
| 3,860,173 A | 1/1975 | Sata |
| 4,052,004 A | 10/1977 | Martin et al. |
| 4,085,893 A | 4/1978 | Durley, III |
| 4,153,201 A | 5/1979 | Berger et al. |
| 4,251,031 A | 2/1981 | Martin et al. |
| 4,271,705 A | 6/1981 | Crostack |
| 4,294,407 A | 10/1981 | Reichl et al. |
| 4,301,093 A | 11/1981 | Eck |
| 4,301,968 A | 11/1981 | Berger et al. |
| 4,309,989 A | 1/1982 | Fahim |
| 4,319,155 A | 3/1982 | Nakai et al. |

(List continued on next page.)

FOREIGN PATENT DOCUMENTS

| | | |
|---|---|---|
| EP | 0 156 4009 A2 | 2/1985 |
| EP | 0 437 155 B1 | 2/1990 |
| EP | 0 657 226 B1 | 11/1994 |
| GB | 2 099 710 A | 12/1982 |
| GB | 2 101 500 A | 1/1983 |
| JP | 2000237275 A2 | 9/2000 |
| WO | WO 96/35383 | 11/1996 |

OTHER PUBLICATIONS

Journal of Burn Care & Rehabilitation; vol. 21, No. 4; Jul./Aug. 2000 pp. 333–338.

Design and Application of Low–Frequency Ultrasound and Its Combination With Laser Radiation in Surgery and Therapy—Critical Reviews in Biomedical Engineering; 2001; pp. 502–519.

*Primary Examiner*—Henry Bennett
*Assistant Examiner*—Sabrina Dagostino
(74) *Attorney, Agent, or Firm*—Carter, DeLuca, Farrell & Schmidt, LLP (57) ABSTRACT

The method and device of the present invention for wound treatment with a combination of laser and ultrasound waves comprises a probe to produce a laser beam and transducer to produce ultrasonic waves. The ultrasonic transducer has tip with a distal end comprising a radiation surface. A liquid is directed to the radiation surface wherein an directed atomized particle spray of the liquid is created upon contact of the liquid with the radiation surface. The laser beam and spray directed to the wound from at least 0,1 inches transmits ultrasound waves as well as particles and has an radiation, irrigation, mechanical cleansing, liquid energizing and bactericide effect on the wound.

45 Claims, 5 Drawing Sheets

U.S. PATENT DOCUMENTS

| | | |
|---|---|---|
| 4,334,531 A | 6/1982 | Reichl et al. |
| 4,352,459 A | 10/1982 | Berger et al. |
| 4,428,531 A | 1/1984 | Martin |
| 4,466,571 A | 8/1984 | Muhlbauer |
| 4,530,360 A | 7/1985 | Duarte |
| 4,541,564 A | 9/1985 | Berger et al. |
| 4,582,654 A | 4/1986 | Karnicky et al. |
| 4,619,400 A | 10/1986 | Van Der Burgt |
| 4,642,581 A | 2/1987 | Erickson |
| 4,655,393 A | 4/1987 | Berger |
| 4,659,014 A | 4/1987 | Soth et al. |
| 4,679,551 A | 7/1987 | Anthony |
| 4,726,523 A | 2/1988 | Kokubo et al. |
| 4,726,525 A | 2/1988 | Yonekawa et al. |
| 4,733,820 A | 3/1988 | Endo et al. |
| 4,756,478 A | 7/1988 | Endo et al. |
| 4,783,003 A | 11/1988 | Hirabayashi et al. |
| 4,790,479 A | 12/1988 | Matsumoto et al. |
| 4,793,339 A | 12/1988 | Matsumoto et al. |
| 4,850,534 A | 7/1989 | Takahashi et al. |
| 4,877,989 A | 10/1989 | Drews et al. |
| 4,905,671 A | 3/1990 | Senge et al. |
| 4,930,700 A | 6/1990 | McKown |
| 4,941,618 A | 7/1990 | Hildebrand et al. |
| 4,961,885 A | 10/1990 | Avrahami et al. |
| 5,002,059 A | 3/1991 | Crowley et al. |
| 5,040,537 A | 8/1991 | Katakura |
| 5,063,922 A | 11/1991 | Hakkinen |
| 5,076,266 A | 12/1991 | Babaev |
| 5,104,042 A | 4/1992 | McKown |
| 5,115,805 A | 5/1992 | Bommannan et al. |
| 5,134,993 A | 8/1992 | van der Linden et al. |
| 5,163,433 A | 11/1992 | Kagawa et al. |
| 5,172,692 A | 12/1992 | Kulow et al. |
| 5,186,162 A | 2/1993 | Talish et al. |
| 5,197,946 A | 3/1993 | Tachibana |
| 5,211,160 A | 5/1993 | Talish et al. |
| 5,231,975 A | 8/1993 | Bommannan et al. |
| 5,269,291 A | 12/1993 | Carter |
| 5,315,998 A | 5/1994 | Tachibana et al. |
| 5,316,000 A | 5/1994 | Chapelon et al. |
| 5,318,014 A | 6/1994 | Carter |
| 5,323,769 A | 6/1994 | Bommannan et al. |
| 5,324,255 A | 6/1994 | Passafaro et al. |
| 5,345,940 A | 9/1994 | Seward et al. |
| 5,347,998 A | 9/1994 | Hodson et al. |
| 5,362,309 A | 11/1994 | Carter |
| 5,374,266 A | 12/1994 | Kataoka et al. |
| 5,380,411 A | 1/1995 | Schlief |
| 5,393,296 A | 2/1995 | Rattner |
| 5,437,606 A | 8/1995 | Tsukamoto |
| 5,515,841 A | 5/1996 | Robertson et al. |
| 5,515,842 A | 5/1996 | Ramseyer et al. |
| 5,516,043 A | 5/1996 | Manna et al. |
| 5,520,166 A | 5/1996 | Ritson et al. |
| 5,520,612 A | 5/1996 | Winder et al. |
| 5,527,350 A | 6/1996 | Grove et al. |
| 5,529,572 A | 6/1996 | Spector |
| 5,545,124 A | 8/1996 | Krause et al. |
| 5,551,416 A | 9/1996 | Stimpson et al. |
| 5,554,172 A | 9/1996 | Horner et al. |
| 5,556,372 A | 9/1996 | Talish et al. |
| 5,573,497 A | 11/1996 | Chapelon |
| 5,616,140 A | 4/1997 | Prescott |
| 5,626,554 A | 5/1997 | Ryaby et al. |
| 5,643,179 A | 7/1997 | Fujimoto |
| 5,656,016 A | 8/1997 | Ogden |
| 5,658,323 A | 8/1997 | Miller |
| 5,699,805 A | 12/1997 | Seward et al. |
| 5,707,402 A | 1/1998 | Heim |
| 5,707,403 A | 1/1998 | Grove et al. |
| 5,730,705 A | 3/1998 | Talish et al. |
| 5,735,811 A | 4/1998 | Brisken |
| 5,743,863 A | 4/1998 | Chapelon |
| 5,752,924 A | 5/1998 | Kaufman et al. |
| 5,762,616 A | 6/1998 | Talish |
| 5,785,972 A | 7/1998 | Tyler |
| 5,835,678 A | 11/1998 | Li et al. |
| 5,843,139 A | 12/1998 | Goedeke et al. |
| 5,879,314 A | 3/1999 | Peterson et al. |
| 5,879,364 A | 3/1999 | Bromfield et al. |
| 5,882,302 A | 3/1999 | Driscoll, Jr. et al. |
| 5,894,841 A | 4/1999 | Voges |
| 5,947,921 A | 9/1999 | Johnson et al. |
| 5,960,792 A | 10/1999 | Lloyd et al. |
| 5,989,245 A | 11/1999 | Prescott |
| 6,001,069 A | 12/1999 | Tachibana et al. |
| 6,014,970 A | 1/2000 | Irvi et al. |
| 6,024,718 A | 2/2000 | Chen et al. |
| 6,026,808 A | 2/2000 | Armer et al. |
| 6,027,495 A | 2/2000 | Miller |
| 6,041,253 A | 3/2000 | Kost et al. |
| 6,061,597 A | 5/2000 | Rieman et al. |
| 6,076,519 A | 6/2000 | Johnson |
| 6,083,159 A | 7/2000 | Driscoll, Jr. et al. |
| 6,095,141 A | 8/2000 | Armer et al. |
| 6,098,620 A | 8/2000 | Lloyd et al. |
| 6,102,298 A | 8/2000 | Bush et al. |
| 6,106,547 A | 8/2000 | Huei-Jung |
| 6,113,558 A | 9/2000 | Rosenschein et al. |
| 6,113,570 A | 9/2000 | Siegel et al. |
| RE36,939 E | 10/2000 | Tachibana et al. |
| 6,158,431 A | 12/2000 | Poole |
| 6,176,839 B1 | 1/2001 | DeLuis et al. |
| 6,186,963 B1 | 2/2001 | Schwarze et al. |
| 6,190,315 B1 | 2/2001 | Kost et al. |
| 6,190,336 B1 | 2/2001 | Duarte et al. |
| 6,206,842 B1 | 3/2001 | Tu et al. |
| 6,206,843 B1 | 3/2001 | Iger et al. |
| 6,231,528 B1 | 5/2001 | Kaufman et al. |
| 6,234,990 B1 | 5/2001 | Rowe et al. |
| 6,251,099 B1 | 6/2001 | Kollias et al. |
| 6,273,864 B1 | 8/2001 | Duarte et al. |
| 6,321,109 B2 | 11/2001 | Duarte et al. |
| 6,322,527 B1 | 11/2001 | Talish |
| 6,325,769 B1 | 12/2001 | Klopotek |
| 6,413,255 B1 * | 7/2002 | Stern .................... 606/41 |
| 6,423,076 B1 * | 7/2002 | Cardwell et al. ........... 606/130 |

* cited by examiner

WOUND TREATMENT METHOD AND DEVICE WITH COMBINATION OF ULTRASOUND AND LASER ENERGY

This application is a Continuation-In-Part of U.S. application Ser. No. 09/745,943 filed on Dec. 22, 2000 now U.S. Pat. No. 6,533,803, by Eilaz Babaev, entitled: WOUND TREATMENT METHOD AND DEVICE WITH COMBINATION OF ULTRASOUND AND LASER ENERGY, the entire contents of which are hereby incorporated by reference.

FIELD OF INVENTION

The present invention relates to the treatment of wounds using ultrasound and laser energy. In particular, the present invention relates to a method of spraying liquid drugs to the wound surface using ultrasonic waves for delivering drugs, killing bacteria, cleansing a surface, and stimulating healthy tissue cells and treating wound with laser energy.

BACKGROUND OF THE INVENTION

Ultrasonic waves and laser beams have been widely used in medical applications, including diagnostics and therapy, as well as many industrial applications. Diagnostic use of ultrasound waves includes using ultrasonic waves to detect underlying structures in an object or human tissue. In this method, an ultrasonic transducer is placed in contact with the tissue (or object) via a coupling medium and high frequency (1–10 MHz) ultrasonic waves are directed into the tissue. Upon contact with the various underlying structures, the waves are reflected back to a receiver adjacent the transducer. By comparing the signals of the ultrasonic wave as sent with the reflected ultrasonic wave as received, an image of the underlying structure can be produced. This technique is particularly useful for identifying boundaries between components of tissue and can be used to detect irregular masses, tumors, and the like.

Three therapeutic medical uses of ultrasound waves include aerosol mist production, contact physiotherapy and soft tissue ablation. The ultrasound contact therapy procedure may cause a patient significant discomfort and/or pain and skin may appear raw and damaged. Aerosol mist production makes use of a nebulizer or inhaler to produce an aerosol mist for creating a humid environment and delivering drug to the lungs.

Ultrasonic nebulizers operate by the passage of ultrasound waves of sufficient intensity through a liquid, the waves being directed at an air-liquid interface of the liquid from a point underneath or within the liquid. Liquid particles are ejected from the surface of the liquid into the surrounding air following the disintegration of capillary waves produced by the ultrasound. This technique can produce a very fine dense fog or mist. Aerosol mists produced by ultrasound are preferred because a smaller particle size of the aerosol can be obtained with the ultrasonic waves. One of the major shortcomings of ultrasonic inhalers and nebulizers is that there is no directed aerosol to the target. An air stream is then required to direct the aerosol to the target, but this decreases the efficiency of ultrasound.

Ultrasonic sprayers, produced by Sonic and Materials Inc., Misonix Inc., Sono-Tek Inc., Zevex International, Inc., and others, operate by passing liquid through a central orifice of an ultrasound instrument-tip. See, for example, U.S. Pat. Nos. 3,765,606, 4,659,014, 5,104,042, 4,930,700, 4,153,201, 4,655,393, 5,516,043, 5,835,678, 5,879,364 and 5,843,139.

Ultrasonic inhalers and drug delivery systems from Medisonic USA, Inc. 3M, Siemens GmbH, The Procter & Gamble Company, Sheffield Pharmaceuticals, Aradigm, Inc., and others, operate by atomizing liquid using piezoceramic film. See, for example, U.S. Pat. Nos. 4,294,407, 5,347,998, 5,520,166, 5,960,792, 6,095,141, 6,102,298, 6,098,620, 6,026,808 and 6,106,547.

Medical usage of lasers can be divided in several groups: laser blood flow meters (Doppler), tissue ablation, therapy, revasculation and treatment devices, surgery devices, diagnostic device, and others. Medical laser devices from HGM Medical Lasers Inc., Level Laser Medical Systems, Coherent, Inc., ESC Medical Systems, PLC Medical Systems, Inc., Palomar Medical, Altus Medical, Tissue Medical Lasers, Inc. and others, appropriate for the therapy, dermatology, surgery, gynecology, urology, dentistry, veterinary and other applications, operate by atomizing liquid using piezoceramic film. See, for example, U.S. Pat. Nos. 5,374,266, 5,527,350, 5,616,140, 5,707,403, 5,658,323, 6,027,495 and 5,989,245.

OBJECTS OF THE INVENTION

It is an object of the invention to provide an improved method and device for treating wounds.

It is also an object of the invention to provide an improved method and device for treating wounds using a combination of different energy sources, such as ultrasound and laser.

It is a further object of the invention to provide a method and device for delivering a drug, killing bacteria, cleansing a surface and stimulating healthy tissue cell growth.

It is yet a further object of the invention to treat a wound by spraying the surface of the wound with aerosol mist produced by ultrasonic waves and radiating by laser beam.

These and other objects of the invention will become more apparent from the discussion below.

SUMMARY OF INVENTION

The present invention is a method and device using a combination of ultrasonic waves and laser beams to treat wounds. More particularly, the device of the invention creates, directs and delivers ultrasound liquid aerosol spray and a laser beam to the wound surface for delivering drugs, killing bacteria, cleansing the surface, stimulating healthy tissue cells and treating the wound with ultrasound and laser energy. The method of the invention for treating wounds involves the use of a combination of a continuous or pulsed ultrasound waves and a beam of pulsed, scanned or gated continuous wave laser or incoherent radiation.

More particularly the method of the invention comprises producing a directed spray of liquid particles produced by contact of the liquid with a free end surface of an ultrasonic transducer, and the particle spray beam in combination with a laser beam are directed onto the wound. According to the method of the present invention a combination of ultrasonic waves, laser beams and energized medicines (highly activated by ultrasonic waves and laser beams) destroys the surface bacteria and results in a higher level of disinfection by the energized liquids as compared to ordinarily applied liquids. Additionally, the ultrasound and laser energy also stimulate healthy cell growth to aid in granulization and epithelization of healing tissue. Other applications of the method of the invention include non-medical uses, such as cleansing, sterilizing and coating surfaces of objects and food with various agents.

The method of the present invention offers an approach that may re-establish use of some traditional antibiotics and presents a method for fighting bacteria without antibiotics when necessary. The effect of the method of the present invention in highly activating antibiotics may allow some traditional antibiotics to overcome bacteria which have become resistant to that antibiotic. Moreover, independent of the energizing effect on antibiotics, the ultrasonic waves and laser beams which are applied in the method of the present invention also directly physically destroy bacteria. This combined effect has been shown to significantly increase the healing of purulent infected wounds.

This method of wound treatment is particularly advantageous on wounds for which local topical application of a drug is desirable but contact with the wound must be avoided.

The method of the present invention also provides a system of non-contact drug delivery with a combination of laser and ultrasound energy. The wound treatment method is effective when applied to the surface of the wound whether the liquid sprayed is a drug, such as an antibiotic, antiseptic, or equivalent agent, oil, saline, water or a combination of any of the foregoing.

The overall concept of the present invention relates to a method and apparatus for wound treatment using a combination of different energy sources, such as a laser, ultrasound, electric current, magnetic field, ultraviolet, microwaves, radio frequency, and or equivalent sources, as will be apparent to one skilled in this art.

While the invention has been described in general terms, the construction and obvious advantages of the device and method of the present invention will be more clearly understood from the following description of the various specific embodiments when read in conjunction with the accompanying drawings.

DETAILED DESCRIPTION OF THE PREFERRED EMBODIMENTS

Figure 1:
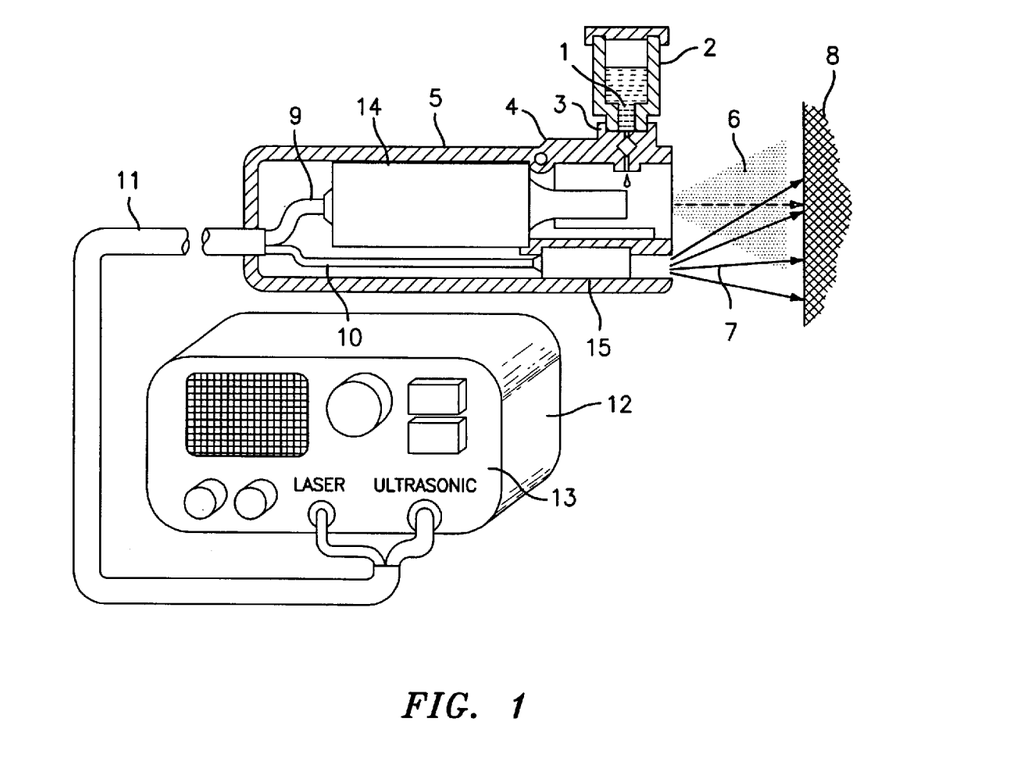
FIG. 1 is a schematic representation of a combined ultrasound and laser wound treatment system for use according to the present invention.

A device for wound treatment according to the present invention is illustrated in FIG. 1, which is a schematic representation of a side elevation of a preferred embodiment of the invention for wound treatment using ultrasound and laser energy. A body 12 has a front panel 13 having various regulatory controls, including controls for controlling on/off, display, intensity and others. Body 12 is connected to a hand piece 5 by an ultrasound cable 9 and a laser cable 10.

Hand piece 5 comprises a laser probe 15, an ultrasound transducer 14, and a liquid reservoir 2. Wound treatment solution 1 from a reservoir 2 is dispensed and delivered by valve 3 to contact the distal end of ultrasound transducer 14 and spray 6 onto the wound surface 8. At the same time, before or after laser source 15 is turned on and radiates the same wound surface 8. More detailed discussion of the operation of the ultrasound transducer can be found in commonly assigned, co-pending U.S. patent application Ser. No. 09/684,044, filed Oct. 6, 2000, and U.S. patent application Ser. No. 09/704,099, filed Nov. 1, 2000, both of which are incorporated herein by reference in there entirety.

Figure 2A:
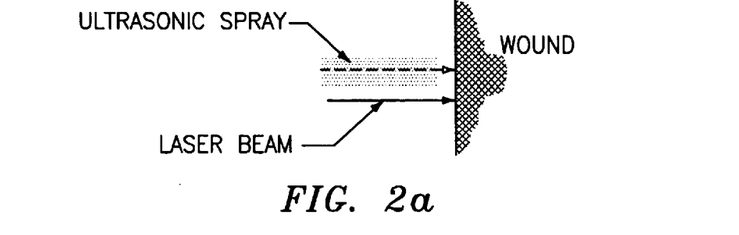
FIG. 2a is a schematic representation of a basic concept of the ultrasonic/laser device of the present invention, showing the ultrasonic spray and laser beams as mutually parallel.
Figure 2B:
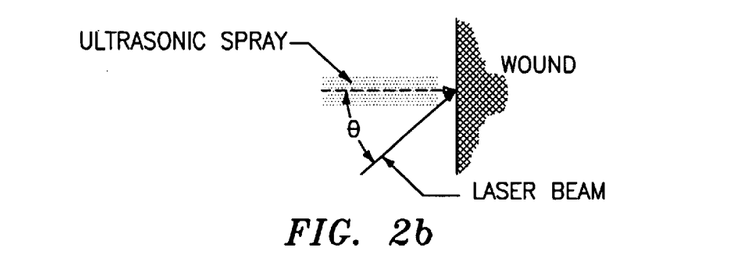
FIG. 2b is a schematic representation of a basic concept of the ultrasonic/laser device of the present invention showing the ultrasonic spray and laser beams as non-parallel.
Figure 2C:
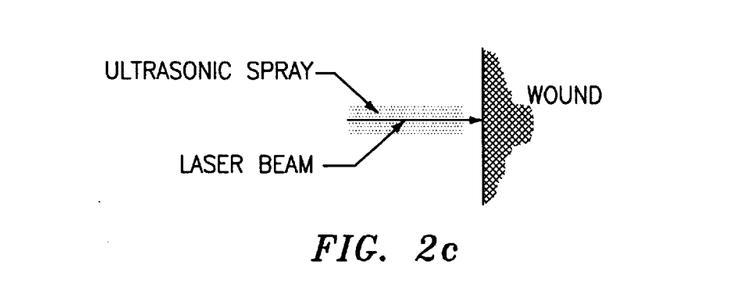
FIG. 2c is a schematic representation of a basic concept of the ultrasonic/laser device of the present invention showing the ultrasonic spray laser beams as coaxial.

FIGS. 2a–2c illustrate the basic concept of ultrasound-laser treatment of a wound according to the present invention. FIG. 2a is a schematic representation of the wound treatment method according to the present invention, where ultrasound spray and laser beam are directed to the wound in parallel. FIG. 2b is a schematic representation of the wound treatment method of the invention showing a coaxial-targeted ultrasound spray and laser beam. FIG. 2c is a schematic representation of the wound treatment according to the invention showing a targeted ultrasound spray and laser beam at an angle to each other.

Figure 3A:
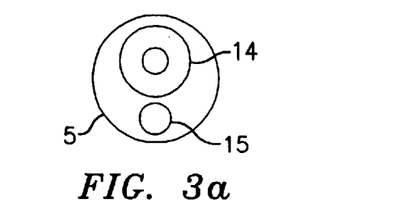
FIGS. 3a–3d are schematic representations of possible variations in the interaction of the laser beam and ultrasonic spray beam of the device depicted in FIG. 1.
Figure 3B:
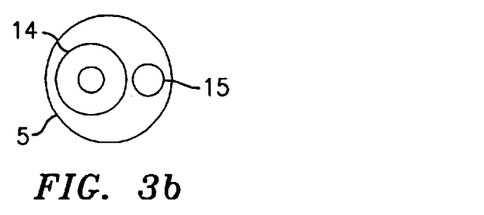
Figure 3C:
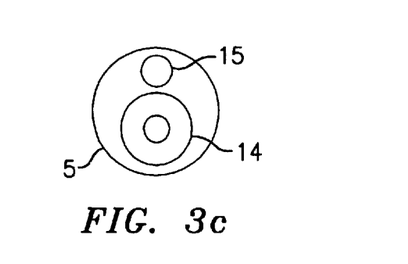
Figure 3D:
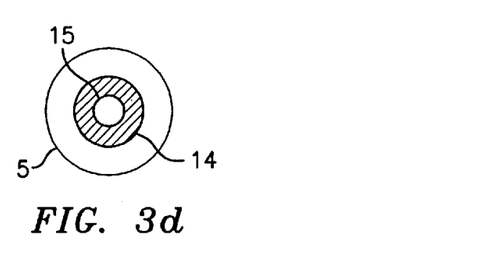

FIGS. 3a–3d depict schematic representations of possible locations of laserprobe 15 and ultrasound transducer 14 relative to main body 5. The preferred location of the laser probe and the ultrasound transducer is shown in FIG. 3a, since it has been determined that this arrangement is most convenient, easy to handle and use. The alternative locations depicted in FIGS. 3b–3d may provide more convenient arrangements in certain applications, as will be apparent to one skilled in this art.

Laser radiation and spray sonication can be activated simultaneously or separately. The preferred treatment method is a simultaneous radiation and sonication procedure, since simultaneous treatment results in a doubling of laser and ultrasonic enhancement effect.

Main body 5 may or may not have disposable parts on the distal end to facilitate ease of use and sterilization.

While the preceding specific embodiments are illustrative of the practice of the invention, it will be understood by one skilled in this art that other expedients known to those skilled in the art or disclosed herein, may be employed without departing from the spirit of the invention or the scope of the appended claims.

The reservoir 2 may be filled with a powder instead of a liquid or in addition to a liquid, from which it is dispensed and delivered by valve 3 or through central orifice (not shown) to contact the distal end of the ultrasound transducer 14 from which it is atomized and delivered as a spray to the wound surface 8.

In another embodiment, ultrasonic energy is delivered to the wound without the use of the spray, i.e., the ultrasonic energy is delivered through a medium other than a spray, including a gaseous medium, such as pure air, e.g., ambient air, where the ultrasound transducer 14 is positioned at a non-contact distance from the wound. The ultrasound waves and the laser beams, even without the use of a spray, destroy surface bacteria and stimulate health cell growth. This method of wound treatment is particularly advantageous on wounds for which contact with the wound should be avoided. The laser energy may be delivered through the spray or through a medium other than the spray, including a gaseous medium, such as pure air.

In another embodiment, a combination of energy sources are provided at a non-contact distance from the wound, where the energy source or sources generate and direct toward the wound one or more of the following forms of energy: laser, ultrasound, electric current, magnetic, ultraviolet, microwave, radio frequency, infrared, coherent radiation, incoherent radiation, X-rays, gamma rays, etc.

Figure 4A:
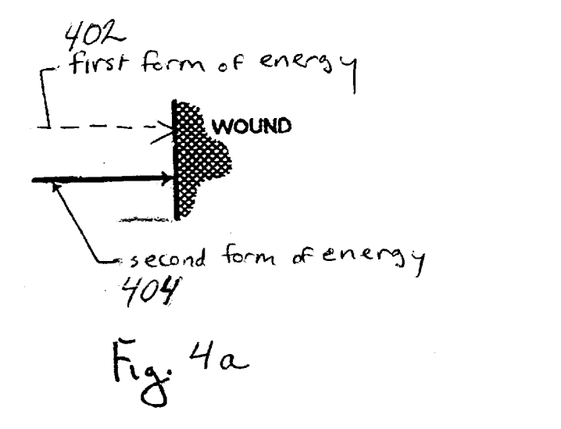
FIG. 4a is a schematic representation of a method of delivery of energy in accordance with one embodiment of the present invention, showing first and second forms of energy.
Figure 4B:
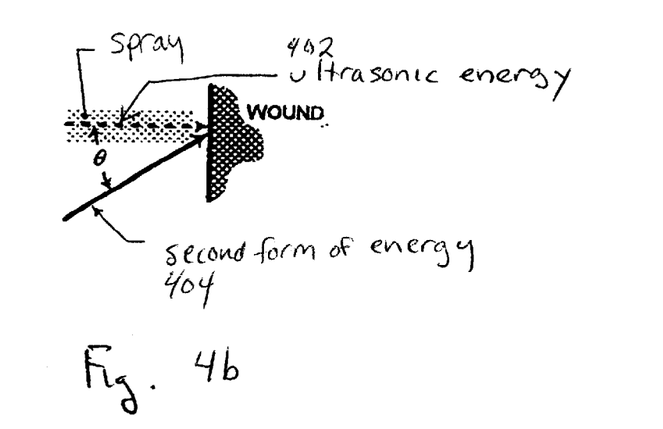
FIG. 4b is a schematic representation of a method of delivery of energy in accordance with another embodiment of the present invention, showing ultrasonic energy delivered through a spray and a second form of energy delivered through pure air.

Preferably, two forms of energy, i.e., first and second forms of energy, are generated from a position that is a non-contact distance from the wound and directed towards the wound for providing a therapeutic and beneficial effect. With reference to FIGS. 4a–c, a combination of first and second forms of energy is shown. In FIG. 4a, the first and second forms of energy, 402 and 404, respectively, are different forms of energy each selected from the group consisting of: laser, ultrasound, electric current, magnetic, ultraviolet, microwave, radio frequency, infrared, coherent radiation, incoherent radiation, X-rays, gamma rays, etc. In FIG. 4b, the first form of energy is ultrasonic energy. A spray directed toward the wound is formed by contacting a liquid or a powder with a radiation surface of an ultrasonic transducer. The ultrasonic energy is delivered to the wound through the spray. Ultrasonic energy may further be delivered to the wound through a medium other than the spray, including a gaseous medium, such as pure air. The second form of energy is selected from the group consisting of: laser, electric current, magnetic, ultraviolet, microwave, radio frequency, infrared, coherent radiation, incoherent radiation, X-rays, gamma rays, etc. and may be delivered through the spray or through a medium other than the spray, including a gaseous medium, such as pure air, at an angle θ with respect to the ultrasonic energy as shown by FIG. 4b, or some other angle.

Figure 4C:
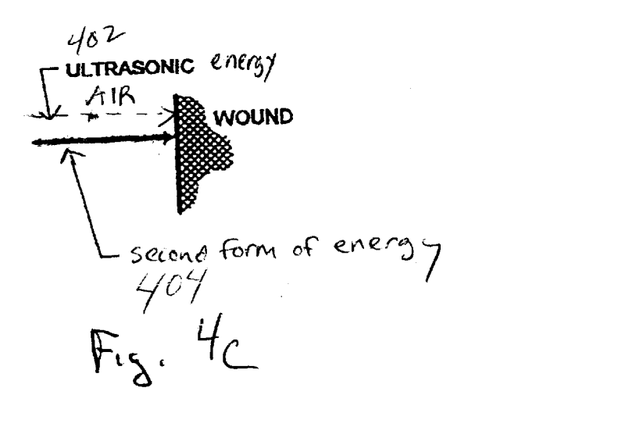
FIG. 4c is a schematic representation of a method of delivery of energy in accordance with a further embodiment of the present invention, showing ultrasonic energy delivered through pure air, and a second form of energy.

In FIG. 4c, the first form of energy is ultrasound, and a liquid or powder is not contacted with the ultrasonic transducer for generating a spray and directing it to the wound. The second form of energy is selected from the group consisting of: laser, ultrasound, electric current, magnetic, ultraviolet, microwaves, radio frequency, infrared, coherent radiation, incoherent radiation, X-rays, gamma rays, etc., where the ultrasonic energy and the second form of energy are delivered through a medium other than a spray, including a gaseous medium, such as pure air.

Figure 5:
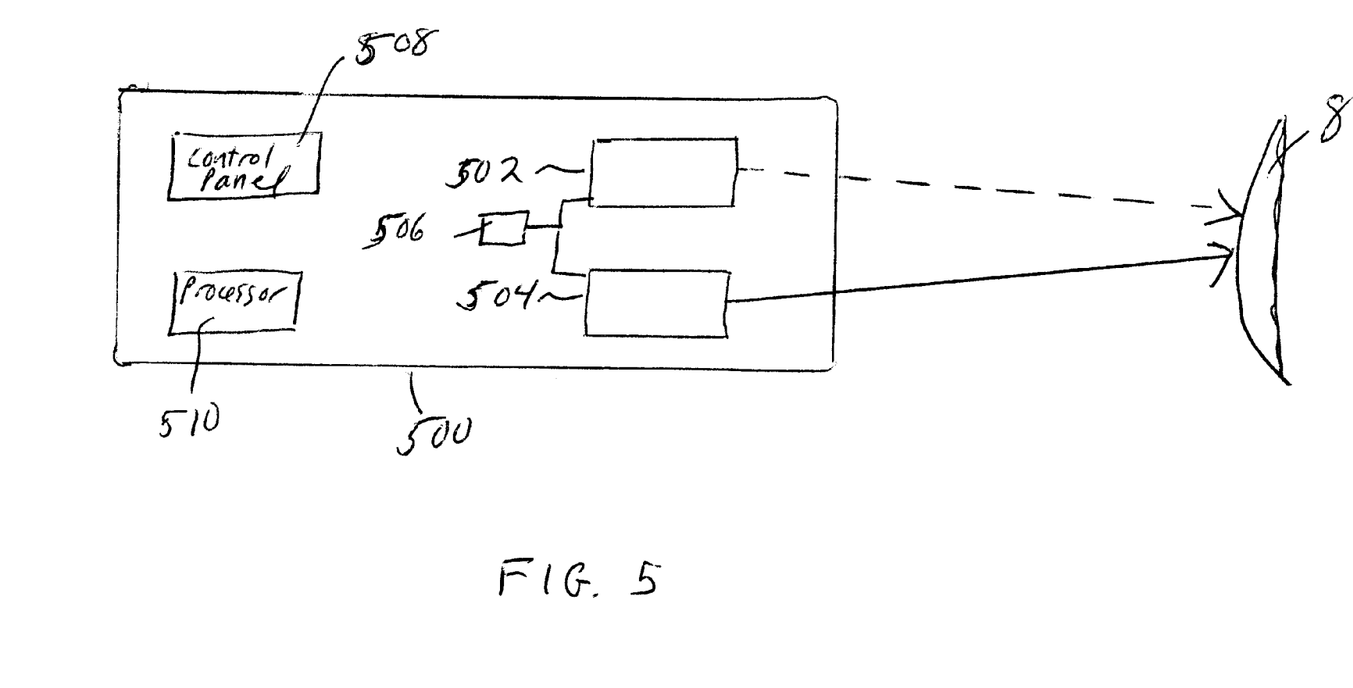
FIG. 5 is a schematic representation of an apparatus having first and second sources of energy directing energy to a wound in accordance with the present invention.

With reference to FIG. 5, an apparatus 500 is shown, where the apparatus 500 includes a first energy source 502 for generating and directing towards the wound 8 the first source of energy, and a second energy source 504 for generating and directing towards the wound 8 the second source of energy. The apparatus 500 and the first and second energy sources 502, 504 may each include one or more individual components, where the individual components are housed in separate housings and connected to each other by couplings, such as electric cables.

A timer 506 is also included within the apparatus 500 for controlling the amount of time each energy source is activated. The timer 506 may successively activate the two energy sources 502, 504 (non-simultaneous activation) or may activate the two energy sources 502, 504 at the same time (simultaneous activation). The timer 506 may be controlled by a user via a control panel 508 or may contain built-in programmable instructions which are executed by a processor 510 of the apparatus 500.

In a preferred embodiment of the invention, wherein the ultrasonic energy is delivered to the wound through a gaseous medium, such as pure air, for achieving a therapeutic effect at the wound, the frequency of the ultrasonic energy generated is selected to be a low frequency so that using the low frequency selected an amplitude of the generated ultrasonic energy is achieved, which is capable of being delivered to the wound with an intensity capable of providing a therapeutic effect to the wound. Preferably the amplitude achieved by the ultrasonic energy is at least 10 microns. Preferably the frequency used is in the range of 20 kHz–50 MHz, wherein a preferred limit is 20–200 kHz, a more preferred limit is 20–40 kHz and a most preferred value is 40 kHz, wherein most preferably the lower limit of the frequency used is outside of the human hearing range. Furthermore, it is advantageous to use a radiation surface having a shape and size selected to achieve delivery of the ultrasonic energy to wound wherein the delivered ultrasonic energy has an intensity capable of providing a therapeutic effect to the wound. Selection of the shape and size of the radiation surface in combination with selection of the frequency and amplitude of the ultrasonic energy used is advantageous in achieving delivery of the ultrasonic energy to the wound wherein the ultrasonic energy has an intensity capable of achieving a therapeutic effect to the wound. Preferably the perimeter radiation surface is round and has a relatively large diameter. Actual selection of the diameter is dependent upon the frequency and amplitude selected. Furthermore, the shape of the radiation surface is selected from one of flat, concave, convex, or a combination thereof.

Figure 6:
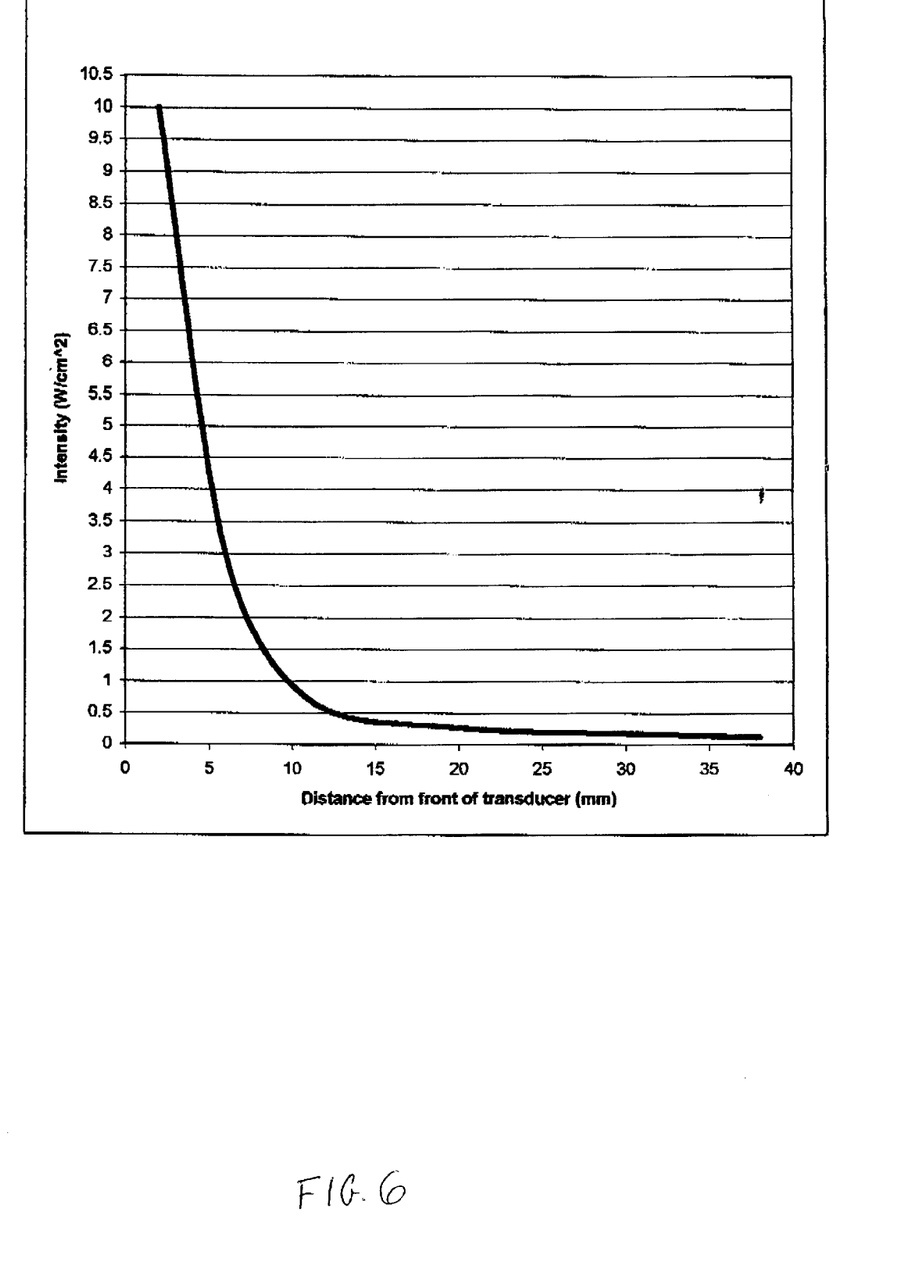
FIG. 6 is a plot of experimental results achieved upon delivering ultrasound energy substantially through air only to a wound in accordance with the present invention.

With respect to FIG. 6, results are shown of experimentation performed in mid-January 2003 at Celleration Acoustic Laboratory, Eden Prairie, Minn. Ultrasonic energy having an intensity capable of providing a therapeutic effect was delivered substantially through air only to a wound using an ultrasound transducer positioned at a non-contact distance from the surface of the wound. The ultrasonic energy was generated at a frequency of 40 kHz and an amplitude of 61 microns. The transducer radiation surface was flat, rounded and had a diameter of 1 cm. Hydrophone Model number PVDF-Z44-1000 and Hydrophone Amplifier Model number A17db, both manufactured by ONDA Corporation, Sunnyvale, Calif., were employed, using an amplifier gain of 7.44. Calibration of the hydrophone was performed by ONDA Corporation. As shown, with the transducer positioned at a distance of between 2.5 mm and 38 mm, ultrasonic energy was delivered to the wound having an intensity capable of providing a therapeutic effect to the wound; the intensity being within the range of 10 W/cm$^2$ and over 0.1 W/cm$^2$.

Although the illustrative embodiments of the present invention have been described herein with reference to the accompanying drawings, it is to be understood that the invention is not limited to those precise embodiments, and that various other changes and modifications may be affected therein by one having ordinary skill in the art without departing from the scope or spirit of the invention. Accordingly, various modifications and variations can be made without departing from the spirit or scope of the invention as set forth in the following claims both literally and in equivalents recognized in law

What is claimed is:

1. An apparatus for treating a wound using ultrasonic energy and another form of energy comprising:
   means for generating ultrasonic energy; and
   means for generating another form of energy, wherein the means for generating the ultrasonic energy and another form of energy include components of a device for generating both the ultrasonic energy and the another form of energy, wherein the means for generating the ultrasonic energy and the another form of energy are positioned at a non-contact distance from the wound, and wherein delivery of the ultrasonic energy and another form of energy to the wound provides a therapeutic effect for decreasing the healing time of the wound.

2. The apparatus according to claim 1, further comprising:
   means for introducing a material to the means for generating ultrasonic energy to generate a spray, wherein at least a portion of the ultrasonic energy is delivered to the wound through the spray.

3. The apparatus according to claim 1, wherein at least one of the ultrasonic energy and another form of energy is delivered to the wound through a gaseous medium.

4. The apparatus according to claim 1, wherein at least one of the ultrasonic energy and another form of energy is delivered to the wound through a spray.

5. The apparatus according to claim 2, wherein the material is one of a fluid and a powder.

6. The apparatus according to claim 1, wherein the another form of energy is selected from the group consisting of: laser, electric current, magnetic, ultraviolet, microwave, radio frequency, infrared light, coherent radiation, incoherent radiation, X-rays, and gamma rays.

7. The apparatus according to claim 1, further comprising means for controlling activation of the means for generating the ultrasonic energy and the means for generating the another form of energy for providing one of simultaneous and non-simultaneous activation thereof.

8. A method for treating a wound using ultrasonic energy combined with an other form of energy, said method comprising the steps of:
   providing an ultrasound transducer at a distance from the surface of the wound for emitting ultrasonic energy;
   generating a spray by contacting a material with a portion of the ultrasound transducer;
   providing a source for generating the other form of energy at a distance from the surface of the wound for emitting the other form of energy;
   delivering the other form of energy to the wound; and
   delivering the ultrasonic energy to the wound through the spray, wherein delivery of the ultrasonic and other form of energy to the wound provides a therapeutic effect for decreasing the healing time of the wound.

9. The method according to claim 8, wherein the step of delivering the other form of energy comprises the step of delivering the other form of energy to the wound through one of the spray and pure air.

10. The method according to claim 8, wherein the material is one of a fluid and a powder.

11. The method according to claim 8, wherein the other form of energy is selected from the group consisting of: laser, electric current, magnetic, ultraviolet, microwave, radio frequency, infrared light, coherent radiation, incoherent radiation, X-rays, and gamma rays.

12. The method according to claim 8, further comprising the step of controlling emission of the ultrasonic energy and the other form of energy for providing one of simultaneous and non-simultaneous emission thereof.

13. An apparatus for treating a wound using ultrasound and laser energy comprising:
   means for generating ultrasonic energy positioned at a non-contact distance from the surface of the wound;
   means for introducing a material to the means for generating ultrasonic energy to generate a spray; and
   means for generating laser energy in the direction of the spray mid at a non-contact distance from the surface of the wound, wherein delivery of the ultrasonic energy and the laser energy to the wound provides a therapeutic effect for decreasing the healing time of the wound.

14. The apparatus according to claim 13, wherein the laser energy is delivered to the wound through one of the spray and a gaseous medium.

15. The apparatus according to claim 13, wherein the material is one of a fluid and a powder.

16. The apparatus according to claim 13, further comprising a means for controlling activation of the means for generating ultrasonic energy and the means for generating laser energy for providing one of simultaneous and non-simultaneous activation thereof.

17. An apparatus for treating a wound using ultrasound and laser energy comprising:
   means for generating ultrasonic energy positioned at a non-contact distance from the surface of the wound; and
   means for generating laser energy positioned at a non-contact distance from the surface of the wound, wherein the means for generating ultrasonic energy and the means for generating laser energy include components of a device for generating both the ultrasonic energy and the laser energy, and wherein combined delivery of the ultrasonic energy and the laser energy to the wound provides a therapeutic effect for decreasing the healing time of the wound.

18. The apparatus according to claim 17, wherein the ultrasonic energy is delivered to the wound through a gaseous medium.

19. The apparatus according to claim 17, wherein the means for generating ultrasonic energy generates ultrasonic waves having a significantly high amplitude for being delivered to the wound such that upon delivery the ultrasonic energy has an intensity capable of achieving the therapeutic effect.

20. The apparatus according to claim 19, wherein the generated ultrasonic energy has a significantly low frequency for achieving the significantly high amplitude.

21. The apparatus according to claim 19, wherein the significantly high amplitude is greater than 10 microns.

22. The apparatus according to claim 20, wherein the significantly low frequency is within the range of 20 kHz–50 MHz for achieving the significantly high amplitude.

23. The apparatus according to claim 20, wherein the significantly low frequency is within the range of 20–200 kHz for achieving the significantly huh amplitude.

24. The apparatus according to claim 20, wherein the significantly low frequency is within the range of 20–40 kHz for achieving the significantly high amplitude.

25. The apparatus according to claim 17, wherein a surface area of a radiation surface of the means for generating ultrasonic energy is significantly large for achieving delivery of ultrasonic energy to the wound having an intensity capable of achieving the therapeutic effect.

26. The apparatus according to claim 17, wherein a perimeter of a radiation surface of the means for generating ultrasonic energy is rounded for achieving delivery of ultrasonic energy to the wound having an intensity capable of achieving the therapeutic effect.

27. The apparatus according to claim 17, wherein a selection is made of at least one of a sue of a surface area of a radiation surface of the means for generating ultrasonic energy, a shape of a peripheral boundary of the radiation surface, a frequency of the ultrasonic energy generated, and an amplitude of the ultrasonic energy generated for achieving delivery of ultrasonic energy to the wound having an intensity capable of achieving the therapeutic effect.

28. The apparatus according to claim 17, wherein a selection is made of a combination of the size of a surface area of a radiation surface of the means for generating ultrasonic energy; a shape of a peripheral boundary of the curvature of the radiation surface; a shape of the radiation surface selected from one of flat, concave, convex and a combination thereof; a frequency of the ultrasonic energy generated; and an amplitude of the ultrasonic energy generated for achieving delivery of ultrasonic energy to the wound having an intensity capable of achieving the therapeutic effect.

29. A method for treating a wound using ultrasound and laser energy comprising:

generating ultrasonic energy from a non-contact distance from the surface of the wound;

generating laser energy from a non-contact distance from the surface of the wound; and delivering the ultrasonic energy and the laser energy to the wound in combination for providing a therapeutic effect for decreasing the healing rime of the wound, wherein the ultrasonic energy and the laser energy are generated by the same device.

30. The method according to claim 29, wherein the delivering step includes delivering the ultrasonic energy to the wound through a gaseous medium.

31. The method according to claim 29, wherein the generating ultrasonic energy step includes generating ultrasonic waves with a significantly high amplitude for being delivered to the wound such that upon delivery the ultrasonic energy has an intensity capable of achieving the therapeutic effect.

32. The method according to claim 31, wherein the generating ultrasonic energy step includes generating the ultrasonic energy with a significantly low frequency for achieving the significantly high amplitude.

33. The method according to claim 29, wherein the generating ultrasonic energy step includes generating the ultrasonic energy from a radiation surface having a significantly large surface area for achieving delivery of ultrasonic energy to the wound having an intensity capable of achieving the therapeutic effect.

34. The method according to claim 29, wherein the generating ultrasonic energy step includes generating the ultrasonic energy from a radiation surface having a rounded peripheral boundary for achieving delivery of ultrasonic energy to the wound having an intensity capable of achieving the therapeutic effect.

35. The method according to claim 29, wherein the generating ultrasonic energy step includes selecting a combination of a size of a surface area of a radiation surface; a shape of a peripheral boundary of the radiation surface; a shape of the curvature of the radiation surface selected from one of flat, concave, convex and a combination thereof; a frequency of the ultrasonic energy; and an amplitude of the ultrasonic energy for achieving delivery of ultrasonic energy to the wound having an intensity capable of achieving the therapeutic effect.

36. An apparatus for treating a wound using first and second forms of energy comprising:

means for generating a first form of energy; and means for generating a second form of energy, wherein the means for generating the first and second forms of energy are positioned at a non-contact distance from the wound, wherein at least one of the first and second forms of energy is delivered to the wound through a spray, and wherein delivery of the first and second forms of energy to the wound provides a therapeutic effect for decreasing the healing time of the wound.

37. The apparatus according to claim 36, wherein the means for generating the first form of energy includes means for generating ultrasonic energy; and further comprising:

means for introducing a material to the means for generating ultrasonic energy to generate a spray, wherein at least a portion of the ultrasonic energy is delivered to the wound through the spray.

38. The apparatus according to claim 36, wherein the first and second forms of energy are selected from the group consisting of: laser, electric current, magnetic, ultraviolet, microwave, radio frequency, infrared light, coherent radiation, incoherent radiation, X-rays, and gamma rays.

39. The apparatus according to claim 36, further comprising means for controlling activation of the means for generating the first form of energy and the means for generating the second form of energy for providing one of simultaneous and non-simultaneous activation thereof.

40. An apparatus for treating a wound using ultrasound and laser energy comprising:

means for generating ultrasonic energy positioned at a non-contact distance from the surface of the wound; and means for generating laser energy at a non-contact distance from the surface of the wound, wherein the means for generating ultrasonic energy and the means for generating laser energy include components housed within the same housing, and wherein delivery of the ultrasonic energy and the laser energy to the wound provides a therapeutic effect for decreasing the healing time of the wound.

41. The apparatus according to claim 40, further comprising means for controlling activation of the means for generating ultrasonic energy and the means for generating laser energy for providing one of simultaneous and non-simultaneous activation thereof.

42. The apparatus according to claim 17, further comprising means for controlling activation of the means for generating ultrasonic energy and the means for generating laser energy for providing one of simultaneous and non-simultaneous activation thereof.

43. The apparatus according to claim 17, wherein the ultrasonic energy is delivered to the wound trough a spray.

44. The apparatus according to claim 40, wherein the ultrasonic energy is delivered to the wound through a gaseous medium.

45. The apparatus according to claim 40, wherein the ultrasonic energy is delivered to the wound through a spray.

* * * * *